United States Patent
Krepinsky et al.

(10) Patent No.: US 6,187,591 B1
(45) Date of Patent: Feb. 13, 2001

(54) SCREENING TEST FOR EARLY DETECTION OF COLORECTAL CANCER

(76) Inventors: Jiri J Krepinsky, 810 Srigley Street, Newmarket, Ontario (CA), L3Y 1X7; Jacek Chociej, deceased, late of Toronto (CA); by Malgorzata Chociej, legal representative, Unit 89 43 Valley Woods Road, Don Mills, Ontario (CA), M3A 2R5

(*) Notice: Under 35 U.S.C. 154(b), the term of this patent shall be extended for 0 days.

(21) Appl. No.: 09/270,103

(22) Filed: Mar. 16, 1999

(30) Foreign Application Priority Data

Nov. 6, 1998 (CA) .................................................. 2253093

(51) Int. Cl.$^7$ .......................... G01N 33/68; G01N 33/53; C12Q 1/26
(52) U.S. Cl. .............................. 436/63; 436/64; 436/166; 436/169; 436/128; 436/164; 435/40.51
(58) Field of Search ................................ 436/63, 64, 166, 436/169, 128, 164; 435/40.51

(56) References Cited

U.S. PATENT DOCUMENTS

| | | |
|---|---|---|
| 4,367,286 | 1/1983 | Saito et al. . |
| 4,762,800 | 8/1988 | Rettig et al. . |
| 4,857,457 | 8/1989 | Shamsuddin et al. . |
| 4,863,854 | 9/1989 | Mattes et al. . |
| 4,962,187 | 10/1990 | Pant . |
| 5,008,184 | 4/1991 | Linnane . |
| 5,073,493 | 12/1991 | Yamashina . |
| 5,162,202 | 11/1992 | Shamsuddin . |
| 5,348,860 | 9/1994 | Shamsuddin . |
| 5,416,025 | 5/1995 | Krepinsky et al. ..................... 436/63 |
| 5,790,761 | * 8/1998 | Heseltine et al. ...................... 395/22 |

OTHER PUBLICATIONS

Biological Abstracts, Abstract XP002130186.
Mendel, J.S., Gastroenterdogy, vol. 97, 592–600 (1989.
Selby, J.V., Annols of Internal Medicine, vol. 118, 1–6 (1993).
Mandel, J.S., New England Journal of Medicine, vol. 328, 1365–1371 (1993).
Lancet, vol. 339, 114–1142 (1992).
Boland, C.R. et al, Proc. Nat. Acad. Sci., vol. 79, 2051–2055 (1982).
Rinderle, S.J. et al, Journal of Biological Chemistry, vol. 264, 16123–16131 (1989).
Sakamoto, K. et al, Cancer Biotherapy, vol. 8, 49–55 (1993).
Lieberman, D.A., American Journal of Gastroenterology, vol. 87, 1085–1093 (1992).
Eddy, D.M., Annals of Internal Medicine, vol. 113, No. 5, 373–384 (1990).
Rex, D.K. et al, Journal of Gastroenterology, vol. 88, No. 6, 825–831 (1993).
Robins, J.H. et al, Canadian Journal of Chemistry, vol. 58, 339–346 (1980).
Kater, F.H., Int. Revs. Cytol., vol. 10, 1 (1960).

* cited by examiner

*Primary Examiner*—Jill Warden
*Assistant Examiner*—Monique T. Cole
(74) *Attorney, Agent, or Firm*—Pillsbury Madison & Sutro LLP

(57) ABSTRACT

A method for detecting neoplasia or cancer of the colon or rectum comprising obtaining a sample of colorectal mucus from the rectum of a patient, and detecting the presence of a marker selected from the group consisting of long chain aliphatic aldehydes containing 12–20 carbon atoms, particularly $CH_3(CH_2)_{14}CHO$ and $CH_3(CH_2)_{16}CHO$; and plasmalogen-bound precursors thereof. Preferably the method comprises treating the sample with Schiff's Reagent and detecting neoplasia or cancer of the colon or rectum based upon the coloration produced at about 560–590 nm in the sample by the treatment. The method does not require the step of adding an enzyme for detecting the disaccharide marker β-D-Gal(1-3)-D-GalNAc(α1-Thr/Ser) and a saccharide marker containing D-galactose and/or 2-acetamido-2-deoxy-D-galactose.

6 Claims, No Drawings

SCREENING TEST FOR EARLY DETECTION OF COLORECTAL CANCER

FIELD OF THE INVENTION

This invention relates to a simple screening test for colorectal cancer whereby a marker is detected in rectal mucus. More particularly, this marker is detected in the mucus deposited on a support using Schiff's reagent.

BACKGROUND OF THE INVENTION

Colorectal carcinoma is the second most frequent cause of cancer mortality in men and women, causing nearly one third of all malignancy-related deaths in North America. It has been estimated that ultimately as many as 6% of Canadians and Americans will develop malignancy in the lower bowel, and over 50% of them will die within 5 years of diagnosis. Many authorities believe that colorectal cancer can be controlled only by preventive measures (1) because there are no realistic prospects of significantly improving the cure rate once the cancer has spread beyond the bowel wall.

Primary prevention, i.e. averting the development of the tumour by altering biological risk factors, is not yet feasible since so little is understood of the etiology of the disease. Alternatively, secondary preventive measures, i.e. detection at an asymptomatic, treatable state, would be possible should an effective screening test be available. Indeed, neoplasms of the lower bowel have the characteristics that make them suitable candidates for the development of a screening test. This is because (i) they are a common cause of cancer-related deaths, and (ii) whereas once the stage of true cancer is reached, and showing symptoms, the mortality rate is over 50%. Removal of bowel neoplasms at their earliest, asymptomatic stage can be done by non-surgical endoscopic polypectomy, without any significant risk. Moreover, it requires at least four to six years before an adenomatous polyp reaches the cancer stage, so there is ample opportunity to detect these neoplasms at their treatable stage. Recent clinical studies document a decrease in mortality in consequence of colorectal cancer screening, as predicted by these theoretical considerations. The problem to-date has been that polyps can be reliably detected only by endoscopy.

Thus, colorectal cancer satisfies each of the following three criteria of a disease considered suitable for a screening program. First, it is a relatively common condition with serious consequences. Second, curative treatment is available when detected at an early stage, i.e. snare polypectomiy through a colonoscope or surgical segmental bowel resection. Third, the prevalence is sufficiently high to justify the expense of a screening program (2).

Principles of Screening

The goal of a medical screening program is to reduce morbidity and mortality by detecting a disease at a sufficiently early stage to allow curative treatment. It is not designed necessarily to diagnose a disease, but to determine which asymptomatic, apparently disease-free individuals should undergo diagnostic interventions. The ability of a screening test to distinguish those who warrant further evaluation from those who do not is expressed in epidemiological terms. The term "sensitivity" is defined as the proportion of diseased individuals who have a positive test, i.e. the proportion of true positives/relative to all persons with the disease. "Specificity" is the proportion of disease-free subjects who have a negative test, i.e. the proportion of true negatives/relative to persons without the disease. The term "positive predictive value" is the proportion of positive tests due to the disease, i.e. the proportion of true positives/ relative to all positives. Almost always, sensitivity and specificity must be traded against each another. Intuitively, it appears wise to design a screening test for a fatal disease so as to optimize sensitivity, in order to detect as many individuals with the disease as possible. It is emphasized, however, that optimizing sensitivity brings with it a risk of reducing specificity to such an extent that unacceptably high costs, poor compliance, and "flooding" of diagnostic facilities result. Moreover, positive predictive value, which is a particularly useful expression of the value of a screening test, is critically dependent on specificity and on the prevalence of the disease in the population screened.

It has been stressed that the effectiveness of a screening test can be properly evaluated only by randomized controlled trials. In the case of cancer, it is not sufficient to demonstrate that life is prolonged when the malignancy is detected by a positive screening test, compared to when the tumour is diagnosed after the development of symptoms. Instead, it must be shown that screened individuals have a lower death rate from the malignancy than similar individuals not enrolled in such a screening program. A particularly fallacious assumption is that the predictive value of a screening test is the same in a hospitalized population with advanced disease, in which the test is usually initially tried, as it is in a healthy population with early minimal disease, to which the test is usually aimed.

Current Population Screening Methods

Endoscopic methods, such as sigmoidoscopy or entire-length colonoscopy, are diagnostic rather than screening techniques, although sigmoidoscopy is sometimes used for screening. The only current method of colorectal cancer screening in the general population is searching for occult blood in the stool (3). Present techniques e.g. HemOccult II which involves smearing a sample of stool onto guaiac-impregnated paper which, after treatment with hydrogen peroxide containing developer, exhibits blue colour if blood (haemoglobin) is present. After almost two decades of experience with this methodology, it has become clear that even in expert centres, the sensitivity is less than 50% for curable neoplasms, and that the positive predictive value approximates, at best, only 40% in a clinic population. An update from the large-scale (n=97, 205) University of Minnesota, Minnesota, United States, prospective trial indicates a positive predictive value for colorectal cancer of only 2.2% (4). Furthermore, factors such as medications, multiple dietary constituents, delays in specimen handling, variabilities in fecal hydration, and storage of assay materials, commonly confound results. Analysis of one of the three randomized controlled studies assessing the value of HemOccult suggests comparable mortality rates in the screened and control populations (5). Newer methods of detecting occult blood, e.g. methods based either on porphyrin analysis [HemoQuant] or antibody specific for human haemoglobin, improve on these results. However, three limiting problems remain unlikely to be overcome. These are that colorectal malignancies shed blood only intermittently, upper gastrointestinal tract bleeding may make the results falsely positive, and multiple lesions in the lower bowel, apart from colorectal neoplasms, commonly bleed. Such lesions include hemorrhoids, diverticulae, ulcers, and vascular ectasie. Compliance in unselected populations has been estimated to be less than 30%, at least partly because the technique requires patients, themselves, to smear their stool onto a slide or a strip, a task most people find not only distasteful, but also technically difficult. Despite this, HemOccult continues to be widely used because the American Cancer Society has recommended occult blood testing yearly for all individuals over 50 years of age, arguing that even an imperfect test will save many lives. Implicit in all arguments over the value of HemOccult is that any improvement in screening techniques for bowel malignancy would have a dramatic impact on colorectal cancer mortality rates, since the screening for occult blood even in the present form leads to reducing mortality from colorectal cancer (6).

Experimental Screening Methods (i) Screening for colorectal cancer by stool DNA analysis (7). This is based on the presence in stool of neoplastic cells shed in large numbers into the colonic lumen. In principle, a mutation which is common to neoplasms could be detected with high precision by analyzing DNA from these cells. Currently, the most common mutation is the K-ras oncogene mutation present in about 40% of colorectal carcinomas and adenomas. Screening for K-ras gene can, therefore, detect, at best, only 40% of all neoplasias. This methodology is at present technically complex and expensive.

(ii) Screening for the presence in colonic mucin of a cancer-related disaccharide, D-Galp($\beta$1-3)-D-GalpNAc($\alpha$1,Ser/Thr), T-(Thomsen-Friedenreich) antigen, since it is widely known that T-antigen is not expressed by cells in healthy colons, whereas it is expressed by cancer (8).

(a) Monoclonal antibodies and lectins: It has been shown that monoclonal antibodies raised against synthetic T-antigen recognize and bind to cancer cells. Similarly, peanut agglutinin (PNA), a lectin, binds strongly to the same disaccharide, but recognizes malignancy with lesser specificity. Amaranthin, a lectin from *Amaranthus caudatus,* has been reported to have better specificity for T-antigen than PNA. Neither amaranthin nor PNA bind to histological sections of normal mucosa, but both bind to mucin in the goblet cells of tumours and certain polyps, and in the transitional mucosa. The visualization of the binding utilizes fluroescently labelled antibodies and lectins (9).

(b) Galactose oxidase test. T-antigen is also reported to be detectable calorimetrically after oxidation of OH-6 of galactose using galactose oxidase and visualization of the resulting aldehyde with Schiff's reagent, —U.S. Pat. No. 4,857,457, issued Aug. 15, 1989; U.S. Pat. No. 5,348,860, issued Sep. 20, 1994; and U.S. Pat. No. 5,162,202, issued Nov. 10, 1992, to Shamsuddin et al. In contrast with the tests using lectins, this test is performed on mucus samples obtained by digital rectal examination and smeared onto a support. This system demonstrated a sensitivity of 74% and specificity of 50% for colorectal neoplasms, i.e. adenomatous polyps and cancer, in one study with only 1 false negative result among 59 patients with cancer. Subsequently, a number of reports of basically the same test has appeared with sensitivity ranging from 35% to 100% and specificity ranging from 15% to 76%. Some investigators found that the test was more sensitive, but less specific, than HemOccult. The lesser specificity has been ascribed to the positivity of the test in individuals with certain inflammatory conditions, such as diverticulitis and ulcerative colitis (10).

In contrast to the aforesaid prior art, a colorectal mucus assay not requiring the detection of the disaccharide marker beta-D-Gal(1->3)-D-GalNAc and a saccharide marker containing D-galactose and/or 2-acetamido-2-deoxy-D-galactose has been described in U.S. Pat. No. 5,416,025 to Krepinsky et al., issued May 16, 1995. In this method, a sample of colorectal mucus is treated with Schiff's reagent, without a step of adding an enzyme for detecting the aforesaid disaccharide marker, and detecting the color change in the sample.

The method described in U.S. Pat. No. 5,416,025 demonstrated a sensitivity of 92% for colorectal cancer from a test with 25 cancer patients. However, specificity is somewhat compromised in that varying shades of pink coloration are often obtained and result in some false positives.

Although the screening test disclosed in U.S. Pat. No. 5,416,025 provides a significant improvement over aforesaid prior art methods in not requiring an enzyme pretreatment step, and a reduction in the relative numbers of false positives and false negative results, it is still desirable to provide a simple assay which further reduces the likelihood of false positive and false negative readings.

REFERENCE LIST

The present specification refers to the following publications, each of which is expressly incorporated herein by reference.

Publications

1. Lieberman D. A.: Targeted colon cancer screening: A concept whose time has almost come. Amer. J. Gastroenterol. 1992, 87, 1085.
2. Eddy D. M.: Screening for colorectal cancer. Ann. Int. Med. 1990, 113, 373.
3. Rex D. K., Lehman G. A., Ulbright T. M., Smith J. J., Pound D. C., Hawes R. H., Helper D. J., Wiersema M. J., Langefeld C. D., Li W.: Colonic neoplasia in asymptomatic persons with negative fecal occult blood tests: influence of age, gender, and family history. Amer. J. Gastroenterol. 1993, 88, 825.
4. Mandel J. S., Bond J. H., Bradley M., Snover D. C., Church T. R., Williams S., Watt G., Schuman L. M., Ederer F., Gilbertsen V.: Sensitivity, specificity, and positive predictivity of the Hemoccult test in screening for colorectal cancer. Gastroenterol. 1989, 97, 597.
5. Selby J. V., Friedman G. D., Quesenberry Jr. C. P., Weiss N. S.: Effect of fecal occult blood testing on mortality from colorectal cancer. Ann. Intern. Med. 1993, 118,1.
6. Mandel J. S., Bond J. H., Church T. R., Snover D. C., Bradley G. M., Schuman L. M., Ederer F.: Reducing mortality from colorectal cancer by screening for fecal occult blood. New Engl. J. Med. 1993, 328, 1365.
7. Editorial: Screening for colorectal cancer by stool DNA analysis. Lancet 1992, 339,1141.
8. Boland C. R,. Montgomery C. K., Kim Y. S.: Alterations in human colonic mucin occurring with cellular differentiation and malignant transformation. Proc. Natl. Acad. Sci. USA 1982, 79, 2051.
9. Rinderle S. J., Goldstein I. J., Matta K. L., Ratcliffe R. M.: Isolation and characterization of Amaranthin, a lectin present in the seeds of Amaranthus caudatus, that recognizes the T-(or cryptic T) antigen. J. Biol. Chem. 1989, 264, 16123.
10. Sakamoto K., Muratani M., Ogawa T., Nagamachi Y.: Evaluation of a new test for colorectal neoplasms: a prospective study of asymptomatic population. Cancer Biotherapy 1993, 8, 49.
11. Robins J. H., Abrams, G. D., Pincock J. A.: The structure of Schiff reagent aldehyde adduct and the mechanism of the Schiff reaction as determined by nuclear magnetic resonance spectroscopy. Can. J. Chem. 1980, 58, 339.
12. Kasten F. H.: The chemistry of Schiff's reagent. Int. Revs. Cytol. 1960, 10, 1.
13. Shamsuddin A.: Diagnostic assays for colon cancer. CRC Press, Boca Raton, Fla. 1991.

Patents
U.S. Pat. No. 4,857,457, Shanisuddin et al Aug. 15, 1989
U.S. Pat. No. 4,762,800, Rettig et al. Aug. 9, 1988
U.S. Pat. No. 4,863,854, Mattes et al. Sept. 5, 1989
U.S. Pat. No. 4,962,187, Pant, Oct. 9, 1990
U.S. Pat. No. 5,073,493, Yamashina, Dec. 17, 1991
U.S. Pat. No. 5,008,184, Linnane, Apr. 16, 1991.
U.S. Pat. No. 5,162,202, Shamsuddin, Nov. 10, 1992
U.S. Pat. No. 5,348,860, Shamsuddin, Sep. 20, 1994
U.S. Pat. No. 5,416,025, Krepinsky et al., May 16, 1995.

SUMMARY OF THE INVENTION

It is an object of the present invention to provide a tool for the screening of asymptomatic persons for cancer of the large bowel and rectum.

It is a further object of the present invention to provide an improved screening test to detect neoplasms of the large bowel and rectum prior to development of a bleeding cancer.

It is a yet further object of the present invention to provide a screening test for colorectal cancer which provides improved specificity.

These and other objects and advantages of the invention will be seen from a reading of the specification as a whole.

Accordingly, the invention provides in one aspect a method for detecting the presence of neoplasia, precancerous condition or cancer of the colon or rectum condition thereof, which method comprises obtaining a sample of colorectal mucus from the rectum of a patient and detecting the presence of a marker selected from the group of long chain aliphatic aldehydes containing 12–20 carbon atoms, optionally, containing olefinic groups; most particularly C16–C18 containing aliphatic aldehydes; and plasmalogen-bound precursors thereof.

More specifically, the invention provides a method for detecting the presence of neoplasia, a precancerous condition or cancer of the large intestine, which comprises:

(a) obtaining a sample of large intestinal mucus from the rectum of a patient;

(b) assaying said sample to detect an aldehyde marker selected from the group consisting of $CH_3(CH_2)_{14}CHO$, $CH_3(CH_2)_{16}CHO$, and precursors thereof; and (c) detecting neoplasia, precancer or cancer of the large intestine based upon the presence of the aldehyde detected in the mucus.

The marker is, preferably, detected immunochemically, and, optionally, quantitatively. The precursors of the markers are believed to be plasmalogen-bound.

The marker is preferably selected from the group consisting octadecanal, common name stearaldehyde, of the formula $CH_3(CH_2)_{16}CHO$, hexadecanal, common name palnitaldehyde, of the formula $CH_3(CH_2)_{14}CHO$, and 9-octadecenal, common name olealdehyde of the formula $CH_3(CH_2)_7CH=CH(CH_2)_7CHO$.

In preferred embodiments of the invention, the knowledge of the structures of the aldehydic markers enables observations of the presence of the aforesaid aldehydes in colorectal mucus utilizing specific properties of the aldehyde group, for example, by polarography or using reagents that specifically react with aldehydic group-forming compounds detectable by their resultant suitable properties, such as color, for example, specific spectral properties, fluorescence, mass spectral, chemi luminescence and other biological reactions detectable by color; and chromatographic properties.

It is believed that the aldehydes are released from acid-sensitive plasmalogens under acidic conditions, and, after their release, immediately react with the reagent. The excess of the unreacted reagent is most preferably removed, for instance by repeated washings with water and/or buffers. Many known aldehyde-detecting compounds and compositions may be of use in the practice of the invention. In particular, compounds containing amino groups that under acidic conditions form with aldehydes, addition compounds endowed with easily detectable properties, such as fluorescence or color. Examples, of such amino group-containing compounds are found in the group of aniline-based dyes. p-Rosanilin is a particularly suitable dye, since after being transformed by reaction with a sulfite or analogues in aqueous hydrochloric acid into colorless Schiff's reagent, the latter reagent reacts with aldehydes with high sensitivity to form a purple colored addition compound defined by absorbance at about $\lambda_{max}$ 560–590 nm. The utilization of p-rosanilin in the form of Schiffs reagent for detection of aldehydes in colorectal mucus is described in more detail, hereinbelow.

Preferably, the method comprises treating said sample with Schiff's reagent and detecting neoplasia or cancer of the colon or rectum based upon the coloration produced at about 560–590 nm $\lambda_{max}$ in said sample by said treatment.

The specific coloration produced according to the practise of the present invention can be visually seen or detected by spectrophotometric determination at about 560 nm. Most preferably, the method does not require the additional step of enzyme treatment for detecting the disaccharide marker beta-D-Gal(1-3)-D-GalNac($\alpha$1-Thr/Ser) and a saccharide marker containing D-galactose and/or 2-acetamido-2-deoxy-D-galactose.

The present invention is based on the discovery that a narrower range of colors obtained by the action of Schiff's reagent on the components of mucus collected from individuals with neoplastic disease of the colorectum can be visually seen or spectrophotometrically measured to better indicate true positives and reject false positives. We have discovered that the mucus collected from such individuals contains detectable amounts of the long chain fatty aliphatic aldehydes $CH_3(CH_2)_{14}CHO$ and $CH_3(CH_2)_{16}CHO$, and the olefinic aldehyde $CH_3(CH_2)_7CH=CH(CH_2)_7CHO$, per se, or are bound within plasmalogens present in the mucus and released therefrom by the acid of the Schiff s reagent. We have found that a purple coloration having a light absorption at about 560–590 nm is produced by the Schiff's reagent with the aforesaid aldehydes. We have found that the mucus of neoplastic disease-free individuals does not provide the visually identifiable color spectrum seen in the mucus, from individuals with neoplastic disease. Further, we have discovered that colorectal mucus contains basic compounds which cause the Schiff's reagent to revert to the originating dye, p-rosanilin; and produce a pink-reddish coloration having a light absorption at 538 nm $\lambda_{max}$. It is often difficult to distinguish this non-desirable coloration from the sought for weak purple coloration, without the need of a color chart, and this, consequently, may lead to an increase in false positives and, thus, reduced specificity of the assay.

We have further discovered that although a number of low molecular weight aliphatic aldehydes are present in colorectal mucus, these aldehydes, some of which contain a carboxylic acid function, by virtue of their solubility in water do not interfere with the assay of the present invention, if, preferably, sufficient aqueous washing of the mucus is carried out.

Thus, in contrast to the above-noted prior art, if water-washing and strict observation of the purple color at about 560–590 nm as the proper indicator of the presence of the high molecular aldehydes and, thus, the presence of a precancerous condition or cancer is maintained, a substantial reduction of false positives, and consequently a substantial increase in the specificity of the test, is obtained.

The purple coloration produced according to the practice of the invention due to the presence of the aforesaid long chain aliphatic fatty aldehydes is distinguishable from the various shades of pink and red coloration caused by other substances present in colorectal mucus remaining in the mucus after aqueous water washing. A color chart enclosed to each kit assists in proper identification of the purple color, even by untrained persons, and thus enables an operator to maintain the high specificity of the test.

It should be noted that the specific purple coloration of value in the practice of the invention does not develop with p-rosanilin alone, although the Schiff's Reagent per se is prepared from p-rosanilin.

We have found that the exact position of $\lambda_{max}$ for a Schiff's Reagent-long chain aldehyde adduct is solvent dependent.

We have found that stearaldehyde—Schiff's Reagent adduct in dichloromethane exhibits a relatively broad absorption maximum at about 590±1 nm, with a shoulder at about 555±1 nm. This adduct in ethanol shows an absorption at about 547 nm with a shoulder at about 578 nm. In the latter solution, the color changed from purple to red which we believe is due to instability of the adduct in ethanol. It is insoluble in water.

P-rosanilin in water has an absorption at about 538 nm, but is insoluble in dichloromethane.

Aldehydes of longer carbon chain length with Schiff's Reagent behave similarly as stearaldehyde adduct. For example, the adduct of myristaldehyde in dichloromethane shows a maximum absorption at about 586 nm with a shoulder at about 556 nm.

Formaldehyde adduct in water gives a broad flat maximum extending from about 560–about 593 nm.

The important advantage of testing rectal mucus, compared to lectin or antibody binding to histological sections of tumor tissue, is the easy accessibility of the material to be tested. Since the luminal surface of the colon is lined throughout its length with mucus, a viscoelastic gel composed of water, electrolytes, organic chemical substances, such as nucleosides and nucleotides, aminoacids, peptides, lipids including phospholipids and products of lipid oxidation, and large molecular weight glycoproteins (mucins), as well as sloughed cells and bacteria, which are movable along the bowel, it is believed that rectal mucus contains mucus from the entire colon, i.e., the mucus secreted by a distal neoplastic tissue flows along the bowel into the rectum at which point it is sampled.

A general procedure of use in the implementation of the invention is as follows.

A mucus sample obtained by a physician or a trained nurse using a gloved finger lubricated with MUKO or a similar lubricant which does not trigger any color change in Schiff's reagent during digital rectal examination from a screened individual is deposited on a suitable water-insoluble substrate or support, such as a pad or a disc. Suitable support materials are prepared from, for example, glass microfibres, some polymer fibres such as polyester fibres and cellulose or modified cellulose fibers. The support may or may not be pretreated with antioxidants such as BHT (butylated hydroxytoluene) or BHA (butylated hydroxyanisol).

The following procedure is preferably employed.

The mucus sample is deposited on a support as described hereinbelow, retained thereon for about 90 minutes before rinsing, or, if taken from a freezer allowed about 90 minutes to thaw. Subsequently, the mucus carrying support is rinsed in 0.1M potassium phosphate buffer, generally for about 10 minutes, twice washed with water for 2 minutes, air dried for 15 minutes to remove the excess water, and the support placed in Schiffs reagent for a short period of time, such as 2 minutes, washed briefly with distilled water, and dried in air. A positive reaction is scored when a purple color appears on the filter within 20–25 minutes after removal from Schiff's reagent.

If a specimen does not produce any coloration, it is either because of the absence of the long chain aliphatic aldehydes or plasmalogen precursors in the mucus, or because mucus was not collected by the gloved finger and, therefore, not deposited on the support. To distinguish between these two possibilities, a negative-testing support is treated with 0.5% periodic acid solution for 5 minutes, rinsed with water, stained with Schiff's reagent for 5 minutes and rinsed again. When mucus lacking the marker is present, purple coloration appears at the place where the mucus was deposited; otherwise the support remains colourless, although some background coloration may develop.

During the practice of the process according to the invention, other colors than purple may be observed, in particular those leaning towards pink and red tones. Such colors reflect the presence of basic substances liberating the original pink-red colored dye p-rosanilin from colorless Schiff's reagent. Since the basic substances noted hereinabove are normally water-soluble, these variations usually indicate that the washing of samples prior to the treatment with Schiffrs reagent was incomplete.

It is known that the properties of Schiff s reagent vary according to the combination of various isomers present in commercial preparations of p-rosanilin and according to the method of preparation of Schiff s reagent itself. However, in contrast to aforesaid prior art, U.S. Pat. No. 5,416,025 to Krepinsky et al., these variations do not exert a significant influence on the test because of the knowledge of the aldehydic nature of the marker and the chemical properties of the adduct between the aldehydes and Schiff s reagent prepared using a suitable procedure. The preferable procedure for the preparation of an appropriate Schiff's Reagent is described hereinbelow. To obtain reproducible results with maximum sensitivity and stability, it is desirable to allow the reagent to mature for between 4 days to 6 weeks in a refrigerator, i.e. at +3°–+5° C., before use.

In a further aspect, the invention provides a screening kit comprising, for example, a container such as a package, carton, tube, box, roll, tape or other capsule-like object comprising a water insoluble substrate capable of adsorbing colorectal mucus and wettable by water and aqueous solutions and by Schiff's reagent.

The substrate may generally be exposed through a suitable circular aperture of, say, for example, 1.0–1.3 cm diameter between two tightly sealed, rectangular, hard plastic plates using double-sided tape. The dimensions of the sealed assembled plates may be those of microscope slides which would enable the utilization of the equipment standard for simultaneous development of microscope slides.

In operation, a physician or a nurse, for example, smears a mucus specimen onto the surface of the support in the plate. The plates are transferred to a laboratory, where they are processed in batches the size of which is determined by the equipment utilized in the practice of the test, for example, of ten plates, as hereinbelow described. The plates are discarded after the results are read.

A procedure is hereinbelow described as a screening test for the early detection of neoplasia of the large bowel and the rectum.

On to the support secured in the plates, as described hereinabove and convenient to handle in a physician's office, is smeared a specimen of mucus obtained during the rectal examination. A suitable lubricant, such as MUKO, for the rectal examination is chosen from among those that do not react with Schiff's reagent. For processing, the following method has been found to be suitable. Individual plates bearing smeared-on mucus specimen are placed into a holder carrying ten plates. The holder is immersed into a vessel containing 0.1M potassium phosphate buffer (pH 7.0) for 10 minutes, while the tank is gently, mechanically vibrated. When vibration is stopped, the holder is lifted from the tank, and the holder is subsequently immersed into a tank containing distilled water and gently vibrated for another two minutes. The water washing is repeated once, the holder is then lifted above the tank, and the excess water allowed to drip back into the tank for ten minutes. The holder with the plates is subsequently immersed into another tank containing Schiff's reagent described hereinbelow, vibrated gently for 2 minutes, then taken out and washed 3 times with distilled water by immersing it in a water-containing tank for 2 minutes in each case. The holder with the plates is then air dried and scored when purple color appears on the support within 20–25 minutes. The minutes are counted from the time of removal from Schiff's reagent. The color is compared with the color chart, and colors other than purple are counted as negative.

Stools deposited on the support together with the mucus may cause an unwanted transformation in the presence of air in the deposited mucus to take place during storage before development, which may result in a false positive test reading. To prevent this transformation from happening, a pretreatment of the mucus-free support may be carried out prior to deposition of mucus with 0.1% solution of an antioxidant, such as, for example, BHT in 95% ethanol., or BHA.

If the test is negative by reason of no color on the support, it is useful to establish if mucus were deposited in the plate. To achieve this objective, the specimen is then treated with periodic acid-Schiff's reagent to determine whether the mucus was deposited on the plate. If the mucus is present, purple color appears. The smear often shows slightly yellow color when mucus is present; colorless deposit usually indicates that only colorless lubricant was deposited.

It should be noted that a weakly positive test result is to be expected if only a small amount of mucus is present on the support, and, thus, it has the same validity as a strongly positive result of an abundant mucus sample.

EXAMPLES

The results obtained, to-date, indicate that some individuals may have presymptomatic malignancy, or a condition increasing the risk of neoplasia. For instance, a segment of inflamed bowel may be transformed into a preneoplastic condition, and this perhaps is detected by the test.

The high sensitivity of the test for neoplasms may reduce the number of patients undergoing colonoscopy because they have rectal bleeding, unexplained iron-deficiency anemia, or a first-degree relative with a tumour.

Example 1

Preparation of the Schiff's reagent

Distilled water (220 mL) is brought to boiling, removed from heat source and p-rosanilin (0.4 g) added. The mixture is stirred well and boiled again for 5 minutes, cooled to 50° C., and the solution filtered through a folded paper filter. 1N hydrochloric acid (34 mL) is added to the filtrate under stirring, and allowed to cool to room temperature. Sodium bisulfite (2.34 g) is added, stirred well and stored at room temperature in a dark place for 4 days. A slightly straw-colored solution is obtained, to which charcoal (NORIT, 300 mg) is added and the mixture vigorously stirred for 1.5 minutes. Subsequently, the solution is filtered through a double paper filter into a dark glass bottle and stored refrigerated at 3–5° C.

Example 2

Patients with Colorectal Cancer and Putative Precancerous Condition.

The sensitivity of the test has been consistently very high since rarely a cancer was missed. However, the specificity measured in the clinical control population is imprecise in patients, who at the moment of the test, have no clinically detected neoplasms but have some other unspecified ailments, which may well predispose to cancer development in the future. Previously, it was shown that the false positive rate among healthy young volunteers—not patients—did not exceed 10.6%. Inflammatory conditions of the large bowel are considered to increase cancer risk. A segment of inflamed bowel may, in fact, be transformed into a preneoplastic condition, and this is, perhaps, detected by the test. Table 1 shows the results of the test performed on mucus from a group of patients from the endoscopy unit of the Wellesley Hospital, some of these patients were diagnosed with colorectal cancer and putative precancerous condition.

TABLE 1

This table shows the results from the endoscopy unit at Wellesley Hospital, Toronto, Ontario, Canada, who agreed to submit themselves to the mucus testing.

| | | Positive | | | Negative | | |
|---|---|---|---|---|---|---|---|
| Condition | Total | # | % | 95% CI* | # | % | 95% CI* |
| Diverticular disease | 4 | 3 | | | 1 | | |
| Adenomatous polyp | 3 | 3 | | | | | |
| Polyp <1cm+ | 21 | 10 | 48 | 26–70 | 11 | 52 | 29–74 |
| Polyp large >1 cm++ | 1 | | | | 1 | | |
| No Neoplasia | 45 | 13 | 29 | 16–44 | 32 | 71 | 56–84 |
| Cancer | 5 | 5 | | | | | |
| Follow up of | | | | | | | |
| cancer removal+++ | 5 | 3 | | | 2 | | |
| Crohn's disease | 2 | 1 | | | 1 | | |
| Ulcerative colitis | 4 | 3 | | | 1 | | |

*CI: confidence interval of percentage positive or percentage negative.
+Less than 1 cm in diameter
++More than 1 cm in diameter
+++removed several weeks before mucus collection.

The following notes provide a better understanding of the Table 1.
(a) The positivity/negativity of the categories except "no neoplasia" reflects the well-known observation that in some individuals these conditions are cancer precursors and some are not. The positivity in the category "no neoplasia" is not explained. However, some positives still may represent a precancerous condition and, thus, not all 13 positives represent a false positive category (see hereinbelow).

(b) No neoplasia includes also: cancer family history (5, 1+, 4−), irritable bowel syndrome (2, 1+, 1−), hemorrhoids (3, 1+, 2−), and angeodisplasia (1, 1−). Adenomatous polyp includes adenoma with diverticulosis (1, 1+). Small polyps include polyps with diverticulosis (2, 2+).

(c) Positivity/negativity of the test in previously removed carcinomas may reflect the completeness of the cancer removal.

(d) Inflammatory conditions are considered a risk factor for colorectal cancer. The positivity in the test may reflect how far an inflammation has progressed to an early stage of cancer.

(e) Percentage and CIs of groups with less than 10 subjects are not calculated.

(f) This test reclassified 8 cases from "positive" to negative by distinguishing more clearly the colour representing "positivity". The 8 cases were in the following categories: 3 "no neoplasia", 1 "cancer family history", 1 "carcinoma previously removed", and 3 "small polyps".

Example 3

Mucus Reaction in Colectomy Specimens with Colorectal Cancer

In order to obtain a sufficient amount of colorectal mucus for chemical identification of the aldehyde marker, the mucus was collected from segments of colon removed from patients with colorectal cancer. At the same time, the presence of the marker using Schiff's reagent was established. The results shown herein confirm the high sensitivity of the test.

Table 2 shows the results on colectomy specimens obtained from the operation theatres of several hospitals in Toronto, Ontario, Canada. The specimens were obtained as follows.

Colectomy specimens 15–20 minutes after surgery were washed with water to remove blood. The mucus was collected by gently scraping the surface with a small spatula without damaging the underlaying mucosa. The scraped mucus was placed into a small plastic vial and frozen. For the assay with Schiff's reagent, the vials were removed from the freezer, allowed to stand at room temperature for 60 minutes to thaw, and a small amount of the mucus on the tip of a spatula was smeared upon the support and assayed.

TABLE 2

| Condition | Total | Pos. # | Pos. % | Pos. CI | Neg. # | Neg. % |
|---|---|---|---|---|---|---|
| Cancer | 15 | 14 | 93.4 | 68–100 | 1* | 6.6 |

*Note that the original color of this mucus specimen was deep green and, therefore, it was difficult to determine the color after the reaction with Schiff's reagent.

Example 4

Isolation and Characterization of Markers

Mucus obtained from human colectomy specimens as described in Example 3 was pooled (66 g) and lyophilized for 24 hours to give a semisolid residue (6.0 g). This residue was consecutively extracted with several solvents and the extracts with chloroform-methanol (2:1) and ethylacetate gave positive reaction with Schiff s reagent. These extracts were combined and subjected to chromatography on a column of silica gel. Chloroform-methanol (7:2.5) afforded a fraction, which after evaporation to dryness gave a residue (36.6 mg) positively reacting with Schiff's reagent. After several chromatographic separations, a highly positively reacting material (4.2 mg) was obtained and further analyzed by NMR spectroscopy. The NMR studies showed that the fraction consisted of a mixture of phospholipids, containing both choline (cf. the signal at $\delta 3.240$ ppm for $—N(CH_3)_3$] and ethanolamine. Hydroxyls in the position 1 and 2 of glycerol were both esterified with fatty acids in about 40% of the compounds. The remaining 60% were esterified only at position 2 of glycerol, while at position 1 was bound an $\alpha,\beta$-unsatured ether, identified through a doublet at $\delta 5.90$ ppm assigned to the vinylic proton O-C$\underline{H}$=CH—. The $\alpha,\beta$-unsaturated ether is a derivative of a higher molecular weight aldehyde, mainly stearaldehyde and palmitaldehyde. The estimate of the ratio between the vinylether containing phospholipids (=plasmalogens) and completely esterified phospholipids as 3:2 was made on the basis of a comparison of signal intensities for CH-2 of the glycerol moiety in plasmalogens at $\delta 5.58$ ppm, the integration of which correlated well with the vinylic signal at $\delta 5.90$ ppm, and in diesterphospholipids at $\delta 5.218$ ppm. The aldehydes were identified by comparison with authentic specimens of O-(2, 3,4,5,6-pentafluorobenzyl) oximes of the aldehydes using mass spectrometry and gas-liquid chromatography. Both aldehydes exhibited M-20 ions instead of molecular ions, m/z 415.1 for palmitaldehyde and m/z 443.2 for stearaldehyde.

The O-(2,3,4,5,6-pentafluorobenzyl) oximes of the aldehydes were prepared from O-(2,3,4,5,6-pentafluorobenzyl) hydroxylamine (250 µL of 0.05M solution in sodium acetate buffer, pH 5) added to the phospholipid mixture (1 mg in 100 µL of water) which was vortexed for 1 minute and allowed to react for 30 minutes. Then 1N HCl (10 µL) was added, and the reaction mixture extracted three time with hexane (1 mL). The combined hexane extracts were dried over sodium sulfate, evaporated to dryness under a stream of nitrogen, and the residue redissolved in hexane (50 µL). This solution (1 µL injections) was used in the gas-liquid chromatography-mass spectrometric identification of the aldehydes.

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

What is claimed is:

1. A method for detecting neoplasia, a precancerous condition or cancer of the colon or rectum comprising obtaining a sample of colorectal mucus from the rectum of a patient and detecting the presence of a marker selected from the group consisting of long chain aliphatic aldehydes containing 12–20 carbon atoms and plasmalogen-bound precursors thereof.

2. A method as defined in claim 1 wherein said aliphatic aldehyde is selected from $CH_3(CH_2)_{14}CHO$ and $CH_3(CH_2)_{16}CHO$.

3. A method for detecting the presence of neoplasia, precancer or cancer of the large intestine, which comprises:
   (a) obtaining a sample of large intestinal mucus from the rectum of a patient;

(b) assaying said sample to detect an aldehyde marker selected from the group consisting of $CH_3(CH_2)_{14}CHO$, $CH_3(CH_2)_{16}CHO$, and plasmalogen-bound precursors thereof; and (c) indicating neoplasia, precancer or cancer of the large intestine based upon the presence of the aldehyde detected in the mucus.

4. A method according to claim 1 wherein the marker is detected immunochemically.

5. A method according to claim 1 wherein the marker is detected quantitatively.

6. A method as defined in claim 1 comprising treating said sample with Schiff's Reagent and detecting neoplasia, a precancerous condition or cancer of the colon or rectum based upon the coloration produced at about 560–590 nm in said sample by said treatment.

* * * * *